US008518913B2

(12) United States Patent
Yuan et al.

(10) Patent No.: US 8,518,913 B2
(45) Date of Patent: Aug. 27, 2013

(54) PHOSPHOROUS DERIVATIVES AS CHEMOKINE RECEPTOR MODULATORS

(75) Inventors: Haiqing Yuan, Irvine, CA (US); Richard I. Beard, Newport Beach, CA (US); Xiaoxia Liu, Lake Forest, CA (US); John E. Donello, Dana Point, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/315,514

(22) Filed: Dec. 9, 2011

(65) Prior Publication Data

US 2012/0157413 A1     Jun. 21, 2012

Related U.S. Application Data

(60) Provisional application No. 61/423,940, filed on Dec. 16, 2010.

(51) Int. Cl.
| | | |
|---|---|---|
| *A61K 31/662* | (2006.01) | |
| *A61K 31/66* | (2006.01) | |
| *A61K 31/675* | (2006.01) | |
| *A61K 31/683* | (2006.01) | |
| *A61P 17/00* | (2006.01) | |
| *A61P 29/00* | (2006.01) | |
| *C07F 9/28* | (2006.01) | |
| *C07F 9/32* | (2006.01) | |
| *C07F 9/40* | (2006.01) | |
| *C07F 9/59* | (2006.01) | |
| *C07F 9/6533* | (2006.01) | |

(52) U.S. Cl.
USPC ............... 514/90; 514/89; 514/117; 544/157; 546/21; 558/190; 562/11; 564/15

(58) Field of Classification Search
None
See application file for complete search history.

(56) References Cited

U.S. PATENT DOCUMENTS

| 5,163,995 A | 11/1992 | Van Heertum |
| 5,177,206 A | 1/1993 | Johnson |
| 7,393,873 B2 | 7/2008 | Anthony |
| 7,622,583 B2 | 11/2009 | Ungashe |
| 7,931,909 B2 | 4/2011 | Hughes |
| 2007/0037794 A1 | 2/2007 | Ungashe |
| 2008/0293720 A1 | 11/2008 | Cleary |

FOREIGN PATENT DOCUMENTS

| DE | 19629144 | 1/1998 |
| EP | 0142152 | 5/1985 |
| EP | 0244097 | 11/1987 |
| EP | 0244098 | 11/1987 |
| EP | 0246749 | 11/1987 |
| EP | 0947500 | 10/1999 |
| EP | 1325920 | 7/2003 |
| WO | WO 03-099773 | 12/2003 |
| WO | WO 2005-004810 | 1/2005 |
| WO | WO 2007-067875 | 6/2007 |
| WO | WO 2008-008374 | 1/2008 |

OTHER PUBLICATIONS

Wydysh et al., Design and Synthesis of Small Molecule Glycerol 3-phosphate Acyltransferase inhibitors, 52 J. Med. Chem. 3317-3327 (2009).*
Vippagunta et al., Crystalline solids, 48 Adv. Drug Delivery Rev. 3-26 (2001).*
Ambati, Jayakrishna et al., "An Animal Model of Age-Related Macular Degeneration in Senescent Ccl-2- or Ccr-2-Deficient Mice," Nature Medicine. vol. 9, No. 11, Nov. 2003.
Beech, John et al., "Neuroprotection in Ischemia-Reperfusion Injury: An Antiinflammatory Approach Using a Novel Broad-Spectrum Chemokine Inhibitor," Journal of Cerebral Blood Flow and Metabolism, vol. 21, 683-689, 2001.
Cross, L.C. et al., "Rules for the Nomenclature of Organic Chemistry," Pure Appli. Chem., 45, 11-30, 1976.
Database CAPLUS Chemical Abstracts Service, 1998, STN No. 1999:104638, vol. 19, No. 12, 1950-1953, 1998.
Fang, I-MO et al., "Expression of Chemokine and Receptors in Lewis Rats With Experimental Autoimmune Anterior Uveitis," Experimental Eye Research, vol. 78, 1043-1055, 2004.
Feria, Manuel et al., "The CCR2 Receptor as a Therapeutic Target," Expert Opin. Ther. Patents, vol. 16, No. 1, 49-57, 2006.
Gerard, Craig et al., "Chemokines and Disease," Nature Immunology, vol. 2, No. 2, 108-115, Feb. 2001.
Grainger, David J. et al., Broad-Spectrum Chemokine Inhibitors (BSCIs) and Their Anti-Inflammatory Effects in Vivo, Biochemical Pharmacology, vol. 65, 1027-1034, 2003.
Keino, Hiroshi et al., "Chemokine and Chemokine Receptor Expression During Experimental Autoimmune Uveoretinitis in Mice," Graefe's Arch. Clin. Exp. Ophthalmol, vol. 241, 111-115, 2003.
Klitgaard, Torben et al., "Chemokine Receptors and Early Activation Markers in Acute Anterior Uveitis," Acta Ophthalmologica Scadinavica, vol. 82, 179-183, 2004.
Masaki, Hidekazu et al., "Structure-Activity Relationship of Benzo(b)thiophene-2-sulfonamide Derivatives as Novel Human Chymase Inhibitors", Bioorganic & Medicinal Chemistry Letters, vol. 13, No. 22, 4085-4088, Nov. 17, 2003.
Meleth, Annal et al., "Serum Inflammatory Markers in Diabetic Retinopathy, " Invest. Ophthalmol Vis. Sci., vol. 46, 4295-4301, 2005.
Patent Cooperation Treaty, Notification of Transmittal of the International Search Report and the Written Opinion of the International Searching Authority, or the Declaration, Form PCT/ISA/220. Int. App. No. PCT/US2011/064233, Feb. 17, 2012.
Reckless, Jill et al., "Identification of Oligopeptide Sequences Which Inhibit Migration Induced by a Wide Range of Chemokines," Biochem. J., vol. 340, 803-811, 1999.
Stahl. Heinrich & Wermuth, Camille (Eds), Handbook of Pharmaceutical Salts, Verlag Helvetica Chemica Acta-Zürich, 329-345, 2002.

(Continued)

*Primary Examiner* — Janet Andres
*Assistant Examiner* — Timothy R. Rozof
(74) *Attorney, Agent, or Firm* — Doina G. Ene

(57) ABSTRACT

The present invention relates to novel phosphorous derivatives, processes for preparing them, pharmaceutical compositions containing them and their use as pharmaceuticals as modulators of chemokine receptors.

14 Claims, No Drawings

(56) References Cited

OTHER PUBLICATIONS

Takeuchi, Aya et al., "CCR5-Deficient Mice Develop Experimental Autoimmune Uveoretinitis in the Context of a Deviant Effector Response," Invest. Ophthalmol Vis. Sci., vol. 46, 3753-3760, 2005.

Tokuyama, Hirotake et al., "The Simultaneous Blockade of Chemokine Receptors CCR2, CCR5 and CXCR3 by a Non-Peptide Chemokine Receptor Antagonist Protects Mice From Dextan Sodium Sulfate-Mediated Colitis," International Immunology, vol. 17, No. 8, 1023-1034, 2005.

Tuallion, Nadine et al., "MCP-1 Expression in Endotoxin-Induced Uveitis," Invest. Ophthalmol Vis. Sci., vol. 43, 1493-1498, 2002.

Wallace, Graham et al.. "The Role of Chemokines and Their Receptors in Ocular Disease," Progress in Retinal and Eye Research, vol. 23, 435-448, 2004.

Weisberg, Stuart et al., "CCR2 Modulates Inflammatory and Metabolic Effects of High-Fat Feeding," J. Clin. Invest., vol. 116, 115-124, 2006.

Wells, Timothy et al., "Chemokine Blockers—Therapeutics in the Making?," Trends in Pharmacological Sciences, vol. 27, No. 1, Jan. 2006.

Yamagami, Satoru et al., "CCR5 Chemokine Receptor Mediates Recruitment of MHC Class II-Positive Langerhans Cells in the Mouse Corneal Epithelium," Invest. Ophthalmol Vis. Sci., vol. 46, 1201-1207, 2005.

Yang, Chang-Hao et al., "Effects of the NF-kB Inhibitor Pyrrolidine Dithiocarbamate on Experimentally Induced Autoimmune Anterior Uveitis," Invest. Ophthalmol Vis. Sci., vol. 46, 1339-1347, 2005.

\* cited by examiner

PHOSPHOROUS DERIVATIVES AS CHEMOKINE RECEPTOR MODULATORS

RELATED APPLICATION

This application claims the benefit of U.S. Provisional Application Ser. No. 61/423,940, filed Dec. 16, 2011, the disclosure of which is hereby incorporated in its entirety herein by reference.

FIELD OF THE INVENTION

The present invention relates to novel phosphorous derivatives, processes for preparing them, pharmaceutical compositions containing them and their use as pharmaceuticals as modulators of chemokine receptors. The invention relates specifically to the use of these compounds and their pharmaceutical compositions to treat disorders associated with chemokine receptor (CCR) modulation.

BACKGROUND OF THE INVENTION

Chemokines are a group of 7- to 14-kd peptides that play an important role in orchestrating leukocyte recruitment and migration during inflammation, and therefore represent an important target for anti-inflammatory therapies (Wells et al., 2006). They act by binding to seven-transmembrane, G protein-coupled receptors, the chemokine receptors. The chemokine system is complex, with about ~50 chemokines and 20 chemokine receptors identified in humans, often acting with redundancy, making selection of specific antagonists difficult (Gerard and Rollins, 2001). Genetic knockout strategies have confirmed the importance of chemokines as regulators of immune function, but the deletion of specific chemokines has led to only specific and relatively mild defects in the inflammatory response further emphasizing the complex redundancy of the system. Selectivity is crucial for use of chemokine receptor antagonists in systemic diseases where a single chemokine-receptor system is implicated such as atherosclerosis where the macrophage/monocyte system is the major player in order to allow a subtle and specific control over immune function (Weisberg et al., 2006; Feria and Diaz Gonzalez et al., 2006).

Many ocular conditions are characterized by inappropriate migration and infiltration of cells such as leukocytes and endothelial cells into the eye with deleterious effects to ocular structures (Wallace et al., 2004). Chemokines have been identified in such diseases and misregulation of the chemokine system is apparent in corneal graft rejection, diabetic retinopathy, age-related macular degeneration (ARMD), chronic inflammatory diseases such as uveitis, dry eye etc. Mice lacking CCR2 or MCP-1 develop features of ARMD with age, including drusen deposits, choroidal neovascularization and photoreceptor atrophy indicating a crucial role for this chemokine and its receptor signaling (Amabati et al., 2003). Thus CCR2 receptor-specific inhibitor might have potential therapeutic benefit in ocular diseases like ARMD. In contrast, various human and animal studies have identified several chemokines in different forms of uveitis, produced both by resident and infiltrating cells, that strongly suggests a prominent role for these molecules in its pathogenesis. Studies in rat and mice models of uveitis have demonstrated up-regulation of monocyte chemoattractant protein-1 (MCP-1), macrophage inflammatory protein-1 (MIP-1), RANTES, stromal derived factor-1 (SDF-1) which are powerful chemoattractants for monocytes and T-cells (Fang et al., 2004; Keino et al., 2003). Similar findings have been reported in peripheral blood mononuclear cells in patients with acute anterior uveitis (AAU), the most common form of human uveitis (Klitgaard et al., 2004). MCP-1 knockout mice and CCR5 knockout mice show reduced endotoxin-induced uveitis, which is the animal model for AAU (Takeuchi et al., 2005; Tuallion et al., 2002). It has also been demonstrated that blocking the chemokine system upstream with the use of NF-κB blockers significantly attenuates experimental AAU in rats (Yang et al., 2005). Blockage of NF-κB results in transcriptional inhibition of multiple chemokines. Given the complexity of pathogenesis in uveitis it is unlikely that a selective inhibition of a chemokine receptor in monotherapy will offer therapeutic benefit. A similar role of multiple chemokines have been shown to be correlated with clinical stage of disease in diabetic retinopathy and dry eye (Meleth et al., 2005; Yamagami et al., 2005). In these ocular diseases the use of broad spectrum chemokine receptor inhibitor which inhibits the function of a wide range of chemokines may be beneficial.

The first broad spectrum chemokine inhibitor (BSCI) to be reported was termed Peptide 3, which was derived from the sequence of human chemokine MCP-1 and was shown to block the migration of monocytes in response to MCP-1, MIP-1, RANTES and SDF-1 (Reckless and Grainger. 1999). A cyclic retro inverse analogue of Peptide 3, constructed of D-amino acids in the reverse sequence, called NR58-3.14.3 was observed to be a more potent chemokine inhibitor (Beech et al., 2001). NR58-3.14.3 has been used to test for anti-inflammatory activities in animal models of atherosclerosis, lung inflammation, irritable bowel syndrome etc (Beech et al., 2001; Grainger and Reckless. 2003; Tokuyama et al., 2005). However there are several disadvantages to using these BSCI as a long-term therapeutic strategy. The known BSCIs which are peptides which have relatively low potency, poor pharmacokinetics, and are unstable in vivo. In addition, systemic use of broad spectrum chemokine receptor inhibitors could potentially lead to deleterious side effects due to their systemic anti-inflammatory activity. However in ocular diseases, a local or topical application would prevent the broad spectrum inhibitor to be taken up systemically. Identification of a small molecule inhibitor of several chemokine receptors could be very useful for treatment of inflammatory ocular diseases. Given the evidence for the role of multiple chemokines in several ocular diseases and these results, we propose that the use of small and large molecule broad spectrum chemokine receptor inhibitors will have utility in the local treatment of ocular inflammatory diseases including, but not limited to, uveitis, dry eye, diabetic retinopathy, allergic eye disease and proliferative retinopathies. Manipulation of multiple chemokines therefore represents a novel therapeutic approach in treating ocular diseases.

WO2008008374 discloses CCR2 inhibitors and methods of use thereof.

WO03/099773 discloses CCR9 inhibitors and methods of use thereof.

U.S. Pat. No. 7,622,583 discloses heteroaryl sulfonamides as antagonists of the CCR2 receptor.

US 2008/0293720 discloses pyridinyl sulfonamide modulators of chemokine receptors.

U.S. Pat. No. 7,393,873 discloses arylsulfonamide derivatives.

SUMMARY OF THE INVENTION

A group of novel phosphorous derivatives which are potent and selective chemokine receptor modulators, has been now discovered. As such, the compounds described herein are useful in treating a wide variety of disorders associated with modulation of chemokine receptors. The term "modulator" as used herein, includes but is not limited to: receptor agonist, antagonist, inverse agonist, inverse antagonist, partial agonist, partial antagonist.

This invention describes compounds of Formula I, which have chemokine receptor biological activity. The compounds in accordance with the present invention are thus of use in medicine, for example in the treatment of humans with diseases and conditions that are alleviated by CCR modulation.

In one aspect, the invention provides a compound having Formula I or a pharmaceutically acceptable salt thereof or stereoisomeric forms thereof, or the individual geometrical isomers, enantiomers, diastereoisomers, tautomers, zwitterions and pharmaceutically acceptable salts thereof:

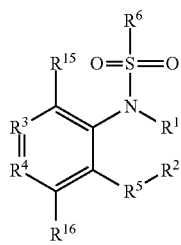

Formula I wherein:
$R^1$ is H or substituted or unsubstituted $C_{1-6}$ alkyl;
$R^2$ is substituted or unsubstituted $C_{1-6}$ alkyl, substituted or unsubstituted $OC_{1-6}$ alkyl, substituted or unsubstituted heterocycle, substituted or unsubstituted $C_{3-8}$ cycloalkyl, substituted or unsubstituted $C_{3-8}$ cycloalkenyl or substituted or unsubstituted $C_{6-10}$ aryl;
$R^3$ is C—$R^7$;
$R^4$ is C—$R^8$;
$R^5$ is —P(O)$R^{10}$;
$R^6$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;
$R^7$ is H, substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl, substituted or unsubstituted $C_{6-10}$ aryl, halogen, substituted or unsubstituted —$OC_{1-6}$ alkyl, CN, $C_{2-6}$ alkenyl, $C_{2-6}$ alkynyl, C(O)$R^{12}$, N$R^{13}R^{14}$ or hydroxyl;
$R^8$ is H, substituted or unsubstituted $C_{1-6}$ alkyl, halogen, —$OC_{1-6}$ alkyl, CN, $C_{2-6}$ alkenyl, $C_{2-6}$ alkynyl or C(O)$R^{12}$;
$R^{10}$ is H, substituted or unsubstituted $C_{1-6}$ alkyl, OH, substituted or unsubstituted $OC_{1-6}$ alkyl or is substituted or unsubstituted HN$C_{1-3}$ alkyl;
$R^{12}$ is H or substituted or unsubstituted $C_{1-6}$ alkyl;
$R^{13}$ is H or substituted or unsubstituted $C_{1-6}$ alkyl;
$R^{14}$ is H or substituted or unsubstituted $C_{1-6}$ alkyl;
$R^{15}$ is H, substituted or unsubstituted $C_{1-6}$ alkyl, halogen, —$OC_{1-6}$ alkyl, CN, $C_{2-6}$ alkenyl, $C_{2-6}$ alkynyl, C(O)$R^{12}$, N$R^{13}R^{14}$ or hydroxyl; and
$R^{16}$ is H, substituted or unsubstituted $C_{1-6}$ alkyl, halogen, —$OC_{1-6}$ alkyl, CN, $C_{2-6}$ alkenyl, $C_{2-6}$ alkynyl, C(O)$R^{12}$, N$R^{13}R^{14}$ or hydroxyl.

In another aspect, the invention provides a compound having Formula I wherein:
$R^1$ is H;
$R^2$ is substituted or unsubstituted $C_{1-6}$ alkyl, substituted or unsubstituted $OC_{1-6}$ alkyl, substituted or unsubstituted heterocycle or substituted or unsubstituted phenyl;
$R^3$ is C—$R^7$;
$R^4$ is C—$R^8$;
$R^5$ is —P(O)$R^{16}$;
$R^6$ is substituted or unsubstituted phenyl;
$R^7$ is H, substituted or unsubstituted $C_{1-6}$ alkyl or halogen;
$R^8$ is H, substituted or unsubstituted $C_{1-6}$ alkyl or halogen;
$R^{10}$ is substituted or unsubstituted $C_{1-6}$ alkyl, OH or substituted or unsubstituted $OC_{1-6}$ alkyl;
$R^{15}$ is H; and
$R^{16}$ is H.

In another aspect, the invention provides a compound having Formula I wherein:
$R^1$ is H;
$R^2$ is substituted or unsubstituted $C_{1-6}$ alkyl, substituted or unsubstituted $OC_{1-6}$ alkyl, substituted or unsubstituted heterocycle or substituted or unsubstituted phenyl;
$R^3$ is C—$R^7$;
$R^4$ is C—$R^8$;
$R^5$ is —P(O)$R^{10}$;
$R^6$ is substituted or unsubstituted phenyl;
$R^7$ is H or halogen;
$R^8$ is H;
$R^{10}$ is substituted or unsubstituted $C_{1-6}$ alkyl, OH or substituted or unsubstituted $OC_{1-6}$ alkyl;
$R^{15}$ is H; and
$R^{16}$ is H.

In another aspect, the invention provides a compound having Formula I wherein:
$R^1$ is H;
$R^2$ is substituted or unsubstituted $C_{1-6}$ alkyl, substituted or unsubstituted $OC_{1-6}$ alkyl, substituted or unsubstituted heterocycle or substituted or unsubstituted phenyl;
$R^3$ is C—$R^7$;
$R^4$ is C—$R^8$;
$R^5$ is —P(O)$R^{10}$;
$R^6$ is substituted or unsubstituted phenyl;
$R^7$ is halogen;
$R^8$ is H;
$R^{10}$ is substituted or unsubstituted $C_{1-6}$ alkyl, OH or substituted or unsubstituted $OC_{1-6}$ alkyl;
$R^{15}$ is H; and
$R^{16}$ is H.

In another aspect, the invention provides a compound having Formula I wherein:
$R^1$ is H;
$R^2$ is n-butoxy, 4-oxopiperidin-1-yl, morpholin-4-yl, phenyl, methyl, 2,5-dimethylphenyl or methoxy;
$R^3$ is C—$R^7$;
$R^4$ is C—$R^8$;
$R^5$ is —P(O)$R^{10}$;
$R^6$ is 4-chloro-3-trifluoromethylphenyl;
$R^7$ is chlorine;
$R^8$ is H;
$R^{10}$ is n-butoxy, OH, ethoxy or methyl;
$R^{15}$ is H; and
$R^{16}$ is H.

The term "alkyl", as used herein, refers to saturated, monovalent or divalent hydrocarbon moieties having linear or branched moieties or combinations thereof and containing 1 to 6 carbon atoms. One methylene (—CH$_2$—) group, of the alkyl can be replaced by oxygen, sulfur, sulfoxide, nitrogen, carbonyl, carboxyl, sulfonyl, or by a divalent $C_{3-6}$ cycloalkyl. Hydrogen atoms on alkyl groups can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, carboxylic acids, ketones, ethers, esters, aldehydes, sulfonamides groups.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by groups including, but not limited to: halogens, —OH, C$_{3-8}$ cycloalkyl, non-aromatic heterocycles, aromatic heterocycles, —OC$_{1-6}$ alkyl, —NH$_2$, —NO$_2$, amides, ethers, esters, carboxylic acids, aldehydes, ketones, sulfonamides groups.

The term "cycloalkenyl", as used herein, refers to a monovalent or divalent group of 3 to 8 carbon atoms, derived from a saturated cycloalkyl having one or more double bonds. Cycloalkenyl groups can be monocyclic or polycyclic. Cycloalkenyl groups can be substituted by groups including, but not limited to: halogens, —OH, C$_{3-8}$ cycloalkyl, non-aromatic heterocycles, aromatic heterocycles, —OC$_{1-6}$ alkyl, —NH$_2$, —NO$_2$, amides, ethers, esters, aldehydes, ketones, carboxylic acids, sulfonamides groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. C$_{2-6}$ alkenyl can be in the E or Z configuration. Alkenyl groups can be substituted by C$_{1-6}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be interrupted by a C═O; the S heteroatom can be oxidized. Heterocycles can be monocyclic or polycyclic. Heterocyclic ring moieties can be substituted by groups including, but not limited to: halogens, —OH, C$_{3-8}$ cycloalkyl, non-aromatic heterocycles, aromatic heterocycles, —OC$_{1-6}$ alkyl, —NH$_2$, —NO$_2$, amides, ethers, esters, aldehydes, carboxylic acids, ketones, sulfonamides groups.

Usually, in the present case, heterocyclic groups are pyridine, furan, azetidine, thiazol, thiophene, oxazol, pyrazol, benzofuran, isoxazole, 2-oxoindoline, 2-oxo-2,3-dihydro-1,3-benzoxazole, 2-oxo-2H-chromene, imidazole[2,1-b]thiazole1-H-pyrazole, indole, imidazole, quinoline, morpholine, piperidine-4-one.

The term "aryl" as used herein, refers to an organic moiety derived from an aromatic hydrocarbon consisting of a ring containing 6 to 10 carbon atoms by removal of one hydrogen. Aryl can be monocyclic or polycyclic Aryl can be substituted by groups including, but not limited to: halogens, —OH, C$_{3-8}$ cycloalkyl, non-aromatic heterocycles, aromatic heterocycles, —OC$_{1-6}$ alkyl, —NH$_2$, —NO$_2$, amides, ethers, esters, carboxylic acids, ketones, aldehydes, sulfonamides groups.

The term "amides" as used herein, represents a group of formula "—C(O)NR$^x$R$^y$" or wherein R$^x$ and R$^y$ are the same or independently H or C$_{1-6}$ alkyl.

The term "ketone" as used herein, represents a group of formula "—C(O)R$^x$" wherein R$^x$ is C$_{1-6}$ alkyl.

The term "ester" as used herein, represents a group of formula "—C(O)OR$^x$" wherein R$^x$ is C$_{1-6}$ alkyl.

The term "ether" as used herein, represents a group of formula "—OR$^x$" wherein R$^x$ is C$_{1-6}$ alkyl.

The term "aldehyde" as used herein, represents a group of formula "—C(O)H".

The term "sulfonamide" as used herein, represents a group of formula "—S(O)$_2$NR$^x$R$^y$" wherein R$^x$ and R$^y$ are the same or independently H or C$_{1-6}$ alkyl.

The term "hydroxyl" as used herein, represents a group of formula "—OH".

The term "amino" as used herein, represents a group of formula "—NH$_2$".

The term "carbonyl" as used herein, represents a group of formula "—C(O)".

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—O—P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:

Ethyl [4-chloro-2-({[4-chloro-3-(trifluoromethyl)phenyl]sulfonyl}amino)phenyl]methylphosphinate;

Dibutyl [4-chloro-2-({[4-chloro-3-(trifluoromethyl)phenyl]sulfonyl}amino)phenyl]phosphonate;

Diethyl (4-chloro-2-(4-chloro-3-(trifluoromethyl)phenyl sulfonamido)phenyl)phosphonate;

Methyl hydrogen [4-chloro-2-({[4-chloro-3-(trifluoromethyl)phenyl]sulfonyl}amino)phenyl]phosphonate;

[4-Chloro-2-({[4-chloro-3-(trifluoromethyl)phenyl]sulfonyl}amino)phenyl]methylphosphinic acid;

4-Chloro-N-{5-chloro-2-[methyl(morpholin-4-yl)phosphoryl]phenyl}-3-(trifluoromethyl)benzenesulfonamide;

4-chloro-N-{5-chloro-2-[methyl(4-oxopiperidin-1-yl)phosphoryl]phenyl}-3-(trifluoromethyl)benzenesulfonamide;

butyl hydrogen [4-chloro-2-({[4-chloro-3-(trifluoromethyl)phenyl]sulfonyl}amino)phenyl]phosphonate;

ethyl hydrogen (4-chloro-2-(4-chloro-3-(trifluoromethyl)phenylsulfonamido)phenyl)phosphonate;

butyl [4-chloro-2-({[4-chloro-3-(trifluoromethyl)phenyl]sulfonyl}amino)phenyl](4-oxopiperidin-1-yl)phosphinate;

ethyl [4-chloro-2-({[4-chloro-3-(trifluoromethyl)phenyl]sulfonyl}amino)phenyl]morpholin-4-ylphosphinate;

methyl [4-chloro-2-({[4-chloro-3-(trifluoromethyl)phenyl]sulfonyl}amino)phenyl](4-oxopiperidin-1-yl)phosphinate;

Ethyl (4-chloro-2-(4-chloro-3-(trifluoromethyl)phenylsulfonamido)phenyl)(phenyl)phosphinate;

ethyl [4-chloro-2-({[4-chloro-3-(trifluoromethyl)phenyl]sulfonyl}amino)phenyl](2,5-dimethylphenyl)phosphinate;

4-chloro-N-[5-chloro-2-(dimethylphosphoryl)phenyl]-3-(trifluoromethyl)benzenesulfonamide;

[4-Chloro-2-({[4-chloro-3-(trifluoromethyl)phenyl] sulfonyl}amino)phenyl]phenylphosphinic acid;

[4-chloro-2-({[4-chloro-3-(trifluoromethyl)phenyl] sulfonyl}amino)phenyl](2,5-dimethylphenyl)phosphinic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the chemokine receptors.

In another embodiment, there are provided pharmaceutical compositions including at least one compound of the invention in a pharmaceutically acceptable carrier.

In a further embodiment of the invention, there are provided methods for treating disorders associated with modulation of chemokine receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by CCR modulation. Therapeutic utilities of CCR modulators are skin inflammatory diseases and conditions, including, but are not limited to: rosacea (dilation of the blood vessels just under the skin), sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases, actinic keratoses, arsenic keratoses, inflammatory and non-inflammatory acne, ichthyoses and other keratinization and hyperproliferative disorders of the skin, eczema, wound healing.

Therapeutic utilities of CCR modulators are ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

In still another embodiment of the invention, there are provided methods for treating disorders associated with modulation of chemokine receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 7,931,909.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of chemokine receptors. Thus, in further embodiments of the invention, there are provided methods for treating a disorder associated with modulation of chemokine receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The described phosphorus derivatives were prepared by methods as shown in Scheme 1. Those skilled in the art will be able to routinely modify and/or adapt Scheme 1 to synthesize any compounds of the invention covered by Formula I.

In one route, an appropriately substituted 2-aniline can react with an aromatic sulfonylchloride to prepare the corresponding sulfonamide. The sulfonamide reacts with ethyl methylphosphinate to form the phosphorous compound of the invention.

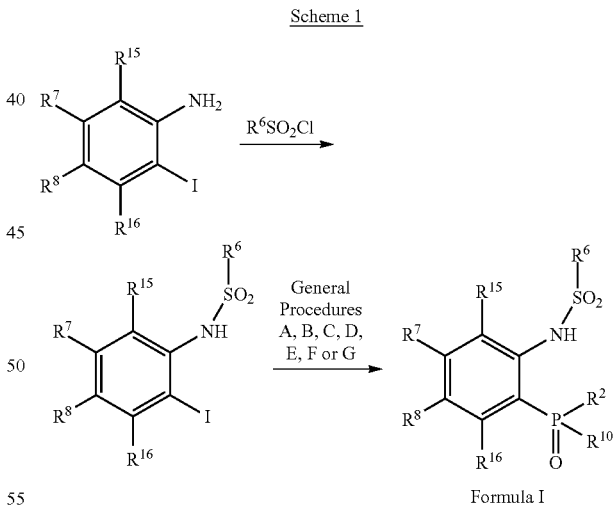

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8 and some intermediates' and reagents' names used in the examples were generated with software such as Chem Bio Draw Ultra version 12.0 or Auto Nom 2000 from MDL ISIS Draw 2.5 SP1. In general, characterization of the compounds is performed according to the following methods:

NMR spectra are recorded on Varian 600 or Varian 300, in the indicated solvent at ambient temperature; chemical shifts in [ppm], coupling constants in [Hz].

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures. Solvents were purchased from commercial sources in appropriate quality and used as received. Air and/or moisture-sensitive reactions were run under an Ar— or $N_2$— atmosphere.

Usually the compounds of the invention were purified by chromatography: CombiFlash Companion and RediSep Rf silica gel 60 (0.04-0.063 mm); Preparative thin layer chromatography (PTLC): Analtech (silica gel 60 $F_{254}$, 500 or 1000 μm). The following abbreviations are used in the examples:
$CH_2Cl_2$ dichloromethane
NaOH sodium hydroxide
MeOH methanol
$CD_3OD$ deuterated methanol
HCl hydrochloric acid
$Na_2SO_4$ sodium sulfate
HBTU 2-(1H-Benzotriazole-1-yl)-1,1,3,3-tetramethyluronium hexafluorophosphate)
CuI copper iodide
$Cs_2CO_3$ caesium carbonate
TMSI N-Trimethylsilylimidazole
DMF dimethylformamide
$MgSO_4$ magnesium sulfate
EtOAc ethyl acetate
$CDCl_3$ deuterated chloroform
$CHCl_3$ chloroform
DMSO-$d_6$ deuterated dimethyl sulfoxide
THF tetrahydrofuran
$K_2CO_3$ potassium carbonate
$N_2$ nitrogen
$NaHSO_3$ sodium bisulfite
$Et_3N$ triethylamine
$SOCl_2$ thionyl chloride
Pd(PPh$_3$)$_4$ Tetrakis(triphenylphosphine)palladium
$Na_2SO_4$ sodium sulfate
TMSBr Bromotrimethylsilane
$Na_2SO_3$ sodium sulfite
MeMgCl methyl magnesium chloride
$D_2O$ deuterated water The following examples are for illustrative purposes only and are not intended, nor should they be construed as limiting the invention in any manner. Those skilled in the art will appreciate that variations and modifications of the following examples can be made without exceeding the spirit or scope of the invention.

Example 1

Intermediate 1

4-Chloro-N-(5-chloro-2-iodophenyl)-3-(trifluoromethyl)benzenesulfonamide

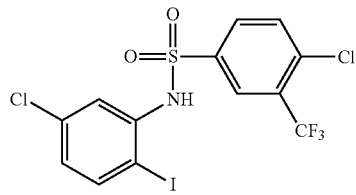 [SMILES: O=S(=O)(Nc1cc(Cl)ccc1I)c1ccc(Cl)c(C(F)(F)F)c1]

A solution of 5-chloro-2-iodoaniline (CAS 6828-35-9) (1.1 g, 4.33 mmol) and 4-chloro-3-(trifluoromethyl)benzenesulfonyl chloride (CAS 32333-53-2) (1.21 g, 4.33 mmol) in pyridine (10 ml) was stirred at 100° C. overnight. The solvent was removed in vacuo and the residue was purified by flash column chromatography on silica gel to afford Intermediate 1 as a light yellow solid (1.3 g, 60%).
$^1$H NMR (300 MHz, $CD_3OD$) δ 8.03 (s, 1H), 7.84-7.93 (m, 1H), 7.68-7.84 (m, 2H), 7.47 (d, J=2.34 Hz, 1H), 7.04 (dd, 1H).

General Procedure A

Example 2

Compound 1

Ethyl [4-chloro-2-({[4-chloro-3-(trifluoromethyl)phenyl]sulfonyl}amino)phenyl]methylphosphinate

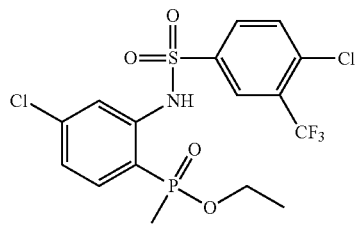 [SMILES: CCOP(C)(=O)c1ccc(Cl)cc1NS(=O)(=O)c1ccc(Cl)c(C(F)(F)F)c1]

A mixture of Intermediate 1 (500 mg, 1.01 mmol), ethyl methylphosphinate (CAS #16391-07-4) (0.3 ml, excess), CuI (10 mg, 0.050 mmol), $Cs_2CO_3$ (657 mg, 2.02 mmol), and N,N'-dimethylethylenediamine (27 mg, 0.30 mmol) in toluene (3 ml) in a sealed tube was heated to 110° C. overnight. The solvent was removed and the residue was purified by flash column chromatography on silica gel (30% ethyl acetate in hexane) to afford Compound 1 (279 mg, 57%).

$^1$H NMR (600 MHz, acetone-$d_6$) δ 11.70 (br. s., 1H), 8.19 (d, J=2.05 Hz, 1H), 8.14 (dd, J=2.35, 8.51 Hz, 1H), 7.93 (d, J=8.51 Hz, 1H), 7.75 (dd, J=2.05, 4.11 Hz, 1H), 7.57 (dd, J=8.36, 13.06 Hz, 1H), 7.26 (dt, J=1.76, 8.22 Hz, 1H), 3.77-3.91 (m, 1H), 3.52-3.67 (m, 1H), 1.63 (d, J=15.26 Hz, 3H), 1.16 (t, 3H).

Compounds 2, 3 and 4 were prepared according to procedure A, as described in Example 2.

Compound 2

Dibutyl [4-chloro-2-({[4-chloro-3-(trifluoromethyl)phenyl]sulfonyl}amino)phenyl]phosphonate

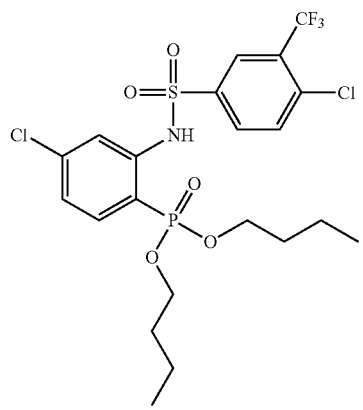 [SMILES: CCCCOP(=O)(OCCCC)c1ccc(Cl)cc1NS(=O)(=O)c1ccc(Cl)c(C(F)(F)F)c1]

Compound 2 (412 mg, 86%) was prepared from Intermediate 1 (423 mg, 0.85 mmol), di-butylphosphite (248 mg, 1.28 mmol), CuI (8 mg, 0.043 mmol), N,N'-dimethyl ethylenediamine (23 mg, 0.26 mmol) and $Cs_2CO_3$ (556 mg, 1.71 mmol) in toluene (3 ml).

$^1$H NMR (300 MHz, $CD_3OD$) δ 7.92-8.29 (m, 2H), 7.83 (d, J=8.20 Hz, 2H), 7.39-7.62 (m, 1H), 7.17-7.39 (m, 1H), 3.64-4.03 (m, 4H), 1.44-1.65 (m, 4H), 1.17-1.40 (m, 4H), 0.88 (t, J=7.33 Hz, 6H).

Compound 3

Diethyl (4-chloro-2-(4-chloro-3-(trifluoromethyl)phenyl sulfonamido)phenyl)phosphonate

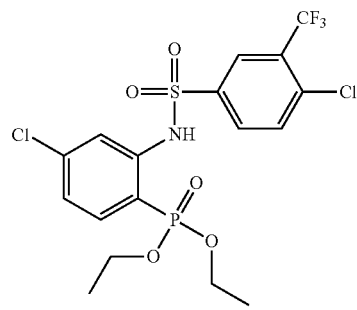 [SMILES: CCOP(=O)(OCC)c1ccc(Cl)cc1NS(=O)(=O)c1ccc(Cl)c(C(F)(F)F)c1]

Compound 3 (184 mg, 50%) was prepared from Intermediate 1 (359 mg, 0.72 mmol), di-ethylphosphite (150 mg, 1.08 mmol), CuI (7 mg, 0.036 mmol), N,N'-dimethyl ethylenediamine (23 mg, 0.26 mmol) and $Cs_2CO_3$ (460 mg, 1.44 mmol) in toluene (3 ml).

$^1$H NMR (300 MHz, $CDCl_3$) δ 10.59 (br. s., 1H), 8.17 (d, J=1.76 Hz, 1H), 7.97 (dd, J=2.05, 8.50 Hz, 1H), 7.79 (dd, J=1.47, 5.57 Hz, 1H), 7.60 (d, J=8.50 Hz, 1H), 7.39 (dd, J=8.35, 13.92 Hz, 1H), 7.12 (dt, J=2.01, 8.28 Hz, 1H), 3.67-4.14 (m, 4H), 1.23 (t, J=7.03 Hz, 6H).

Compound 4

Methyl hydrogen [4-chloro-2-({[4-chloro-3-(trifluoromethyl)phenyl]sulfonyl}amino)phenyl]phosphonate

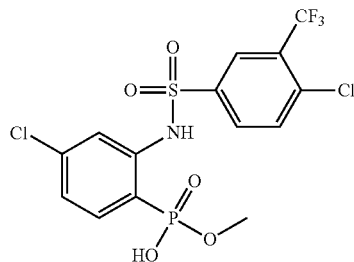 [SMILES: COP(=O)(O)c1ccc(Cl)cc1NS(=O)(=O)c1ccc(Cl)c(C(F)(F)F)c1]

Compound 4 (336 mg, 47%) was prepared from Intermediate 1 (758 mg, 1.53 mmol), dimethyl phosphonate (253 mg, 2.29 mmol), CuI (15 mg, 0.076 mmol), N,N'-dimethylethylenediamine (40 mg, 0.46 mmol) and $Cs_2CO_3$ (996 mg, 3.06 mmol) in toluene (5 ml).

$^1$H NMR (600 MHz, $CD_3OD$) δ 8.13 (d, 1H), 8.04 (dd, J=2.20, 8.36 Hz, 1H), 7.77 (d, J=8.51 Hz, 1H), 7.69 (dd, J=1.76, 4.11 Hz, 1H), 7.57 (dd, J=8.07, 12.77 Hz, 1H), 7.03-7.19 (m, 1H), 3.12 (d, J=11.15 Hz, 3H).

General Procedure B

Example 3

Compound 5

[4-Chloro-2-({[4-chloro-3-(trifluoromethyl)phenyl]sulfonyl}amino)phenyl]methylphosphinic acid

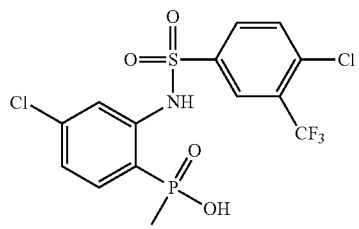 [SMILES: CP(=O)(O)c1ccc(Cl)cc1NS(=O)(=O)c1ccc(Cl)c(C(F)(F)F)c1]

To a solution of Compound 1 (250 mg, 0.525 mmol) in $CHCl_3$ was added TMSI (525 mg, 2.63 mmol) and the mixture was stirred at room temperature for 30 min. The reaction was quenched with water and was extracted with dichloromethane (2×10 ml). The combined organic layer was washed with water, aqueous $NaHSO_3$ and was concentrated. The crude product was purified by flash column chromatography on silica gel (10% MeOH in $CH_2Cl_2$) to give Compound 5 (210 mg, 89%).

$^1$H NMR (600 MHz, $CD_3OD$) δ 8.16 (d, J=2.35 Hz, 1H), 8.05 (dd, J=2.35, 8.51 Hz, 1H), 7.81 (d, J=8.51 Hz, 1H), 7.71

(dd, J=1.76, 4.11 Hz, 1H), 7.54 (dd, J=8.22, 13.21 Hz, 1H), 7.23 (dt, J=1.87, 8.29 Hz, 1H), 1.44 (d, J=15.0 Hz, 3H).

General Procedure C

Example 4

Compound 6

4-Chloro-N-{5-chloro-2-[methyl(morpholin-4-yl) phosphoryl]phenyl}-3-(trifluoromethyl)benzenesulfonamide

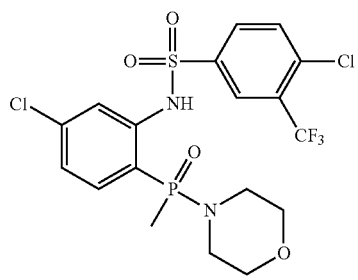 [SMILES: CP(=O)(c1ccc(Cl)cc1NS(=O)(=O)c1ccc(Cl)c(C(F)(F)F)c1)N1CCOCC1]

A mixture of Compound 5 (56 mg, 0.13 mmol), morpholine (11 mg, 0.13 mmol), O-(benzotriazol-1-yl)-N,N,N',N'-tetramethyluronium hexafluorophosphate (HBTU) (47 mg, 0.13 mmol), and di-isopropyl ethyl amine (48 mg, 0.38 mmol) in DMF (2 ml) was stirred at room temperature for 2 days. Water was added and the mixture was extracted with ethyl acetate (2×10 ml). The combined organic layer was washed with brine, dried over $Na_2SO_4$, and concentrated in vacuo. The crude product was purified by flash column chromatography on silica gel (10% MeOH in $CH_2Cl_2$) to give Compound 6 (38 mg, 59%).

$^1$H NMR (600 MHz, $CDCl_3$) δ 11.76 (s, 1H), 8.21 (d, J=1.47 Hz, 1H), 8.03 (dd, J=1.91, 8.36 Hz, 1H), 7.77 (dd, J=1.76, 3.81 Hz, 1H), 7.63 (d, J=8.22 Hz, 1H), 7.21 (dd, J=8.36, 13.35 Hz, 1H), 7.11 (d, J=8.22 Hz, 1H), 3.54-3.70 (m, 4H), 2.85-3.05 (m, 4H), 1.60 (d, J=14.09 Hz, 3H).

Compound 7 was prepared according to procedure C, as described in Example 4.

Compound 7

4-Chloro-N-{5-chloro-2-[methyl(4-oxopiperidin-1-yl)phosphoryl]phenyl}-3-(trifluoromethyl)benzenesulfonamide

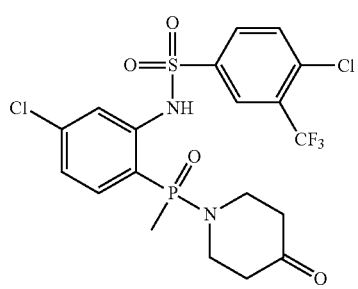 [SMILES: CP(=O)(c1ccc(Cl)cc1NS(=O)(=O)c1ccc(Cl)c(C(F)(F)F)c1)N1CCC(=O)CC1]

Compound 7 (29 mg) was prepared from Compound 5 (50 mg, 0.11 mmol), piperidin-4-one monohydrate hydrochloride (17 mg, 0.11 mmol), O-(benzotriazol-1-yl)-N,N,N',N'-tetramethyluronium hexafluorophosphate (HBTU) (42 mg, 0.11 mmol), and di-isopropyl ethyl amine (43 mg, 0.34 mmol) in DMF (2 ml).

$^1$H NMR (600 MHz, $CDCl_3$) δ 11.72 (br. s., 1H), 8.22 (d, J=1.76 Hz, 1H), 8.04 (dd, J=1.91, 8.36 Hz, 1H), 7.74-7.85 (m, 1H), 7.64 (d, J=8.22 Hz, 1H), 7.19-7.31 (m, 1H), 7.12 (d, J=8.22 Hz, 1H), 3.22-3.40 (m, 4H), 2.34-2.58 (m, J=6.16, 6.16, 17.90 Hz, 4H), 1.70 (d, J=14.09 Hz, 3H).

General Procedure D

Example 5

Compound 8

Butyl hydrogen [4-chloro-2-({[4-chloro-3-(trifluoromethyl)phenyl]sulfonyl}amino)phenyl]phosphonate

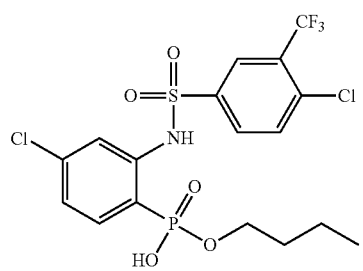 [SMILES: CCCCOP(=O)(O)c1ccc(Cl)cc1NS(=O)(=O)c1ccc(Cl)c(C(F)(F)F)c1]

A solution of Compound 2 (170 mg, 0.30 mmol) in NaOH (5M, 1 ml) was refluxed overnight. The mixture was cooled to room temperature and acidified with 10% HCl (aq.) to pH~1 and then extracted with EtOAc (2×50 ml). The organic layer was washed with brine and dried over $Na_2SO_4$ and concentrated in vacuo. Compound 8 was purified by flash column chromatography on silica gel (0-5% MeOH in EtOAc).

$^1$H NMR (300 MHz, $CD_3OD$) δ 7.89-8.24 (m, 2H), 7.66-7.87 (m, 2H), 7.53 (dd, J=8.35, 13.63 Hz, 1H), 7.13-7.27 (m, 1H), 3.51-3.73 (m, 2H), 1.34-1.53 (m, 2H), 1.12-1.33 (m, 2H), 0.83 (t, J=7.33 Hz, 3H).

Compound 9 was prepared according to procedure D, as described in Example 5.

Compound 9

Ethyl hydrogen (4-chloro-2-(4-chloro-3-(trifluoromethyl)phenylsulfonamido)phenyl)phosphonate

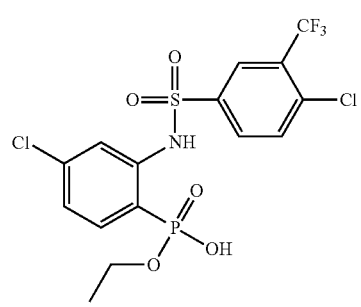 [SMILES: CCOP(=O)(O)c1ccc(Cl)cc1NS(=O)(=O)c1ccc(Cl)c(C(F)(F)F)c1]

Compound 9 (161 mg, 92%) was prepared from Compound 3.

$^1$H NMR (300 MHz, $CD_3OD$) δ 8.21 (d, J=1.76 Hz, 1H), 8.02 (dd, J=2.05, 8.50 Hz, 1H), 7.48-7.72 (m, 3H), 7.05 (dt, J=1.87, 8.28 Hz, 1H), 3.47 (quin, J=7.03 Hz, 2H), 1.00 (t, J=7.03 Hz, 3H).

General Procedure E

Example 6

Compound 10

Butyl [4-chloro-2-({[4-chloro-3-(trifluoromethyl)phenyl]sulfonyl}amino)phenyl](4-oxopiperidin-1-yl)phosphinate

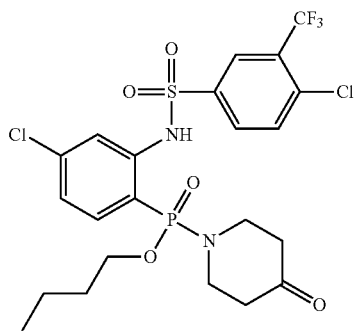 [SMILES: CCCCOP(=O)(c1ccc(Cl)cc1NS(=O)(=O)c1ccc(Cl)c(C(F)(F)F)c1)N1CCC(=O)CC1]

A solution of Compound 8 (65 mg, 0.13 mmol), SOCl$_2$ (1 ml) in CH$_2$Cl$_2$ (1 ml) was refluxed for 2 hours. The solvent was removed and the residue was dried in vacuo. The crude product and piperidin-4-one in Et$_3$N (39 mg, 0.39 mmol) and CH$_2$Cl$_2$ (1 ml) was stirred at room temperature overnight. The solvent was removed and Compound 10 was purified by flash column chromatography on silica gel (5% MeOH in EtOAc).

$^1$H NMR (600 MHz, acetone-d$_6$) δ 11.4 (s, 1H), 8.21 (s, 1H), 8.18 (d, J=8.5 Hz, 1H), 7.95 (d, J=8.5 Hz, 1H), 7.77 (dd, J=1.8, 5.1 Hz, 1H), 7.60 (dd, J=8.2, 13.6 Hz, 1H), 7.24 (d, J=8.3 Hz, 1H), 3.86-4.05 (m, 2H), 3.34-3.40 (m, 4H), 2.32 (t, J=6.0 Hz, 4H), 1.59-1.65 (m, 2H), 1.31-1.39 (m, 2H), 0.88 (t, J=7.33 Hz, 3H).

Compounds 11 and 12 were prepared according to procedure E, as described in Example 6.

Compound 11

Ethyl [4-chloro-2-({[4-chloro-3-(trifluoromethyl)phenyl]sulfonyl}amino)phenyl]morpholin-4-ylphosphinate

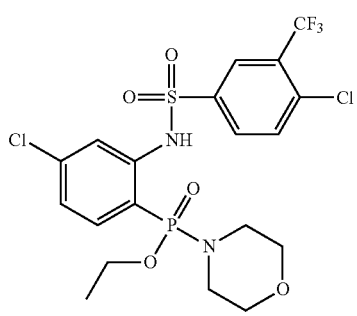 [SMILES: CCOP(=O)(c1ccc(Cl)cc1NS(=O)(=O)c1ccc(Cl)c(C(F)(F)F)c1)N1CCOCC1]

Compound 11 (21 mg) was prepared from Compound 9.

$^1$H NMR (600 MHz, CDCl$_3$): δ (ppm) 10.98 (br. s., 1H), 8.23 (s, 1H), 8.03 (d, J=8.5 Hz, 1H), 7.75 (d, J=5.0 Hz, 1H), 7.63 (d, J=8.5 Hz, 1H), 7.18-7.40 (m, 2H), 7.10 (d, J=8.2 Hz, 1H), 3.77-4.09 (m, 2H), 3.41-3.71 (m, 4H), 2.78-3.18 (m, 4H), 1.12-1.45 (m, J=7.0, 7.0 Hz, 3H).

Compound 12

Methyl [4-chloro-2-({[4-chloro-3-(trifluoromethyl)phenyl]sulfonyl}amino)phenyl](4-oxopiperidin-1-yl)phosphinate

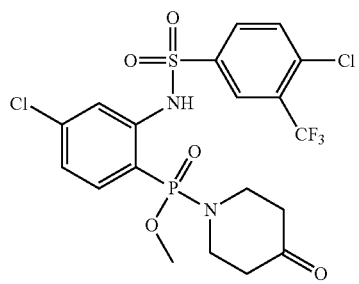 [SMILES: COP(=O)(c1ccc(Cl)cc1NS(=O)(=O)c1ccc(Cl)c(C(F)(F)F)c1)N1CCC(=O)CC1]

Compound 12 (8 mg, 4%) was prepared from Compound 4.

$^1$H NMR (600 MHz, CDCl$_3$) δ 8.22 (d, 1H), 8.03 (dd, J=2.05, 8.51 Hz, 1H), 7.71 (dd, J=1.91, 5.14 Hz, 1H), 7.63 (d, J=8.51 Hz, 1H), 7.32 (dd, J=8.22, 13.50 Hz, 1H), 7.11 (dt, J=2.05, 8.22 Hz, 1H), 3.63 (d, J=11.44 Hz, 3H), 3.27-3.40 (m, 4H), 2.38 (t, J=6.02 Hz, 4H).

General Procedure F

Example 7

Compound 13

Ethyl (4-chloro-2-(4-chloro-3-(trifluoromethyl)phenylsulfonamido)phenyl)(phenyl)phosphinate

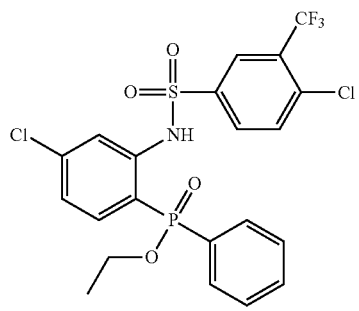 [SMILES: CCOP(=O)(c1ccccc1)c1ccc(Cl)cc1NS(=O)(=O)c1ccc(Cl)c(C(F)(F)F)c1]

A solution of Intermediate 1 (214 mg, 0.43 mmol), ethyl phenylphosphinate (73 mg, 0.43 mmol), Pd(PPh$_3$)$_4$ (50 mg, 0.043 mmol), Et$_3$N (131 mg, 1.29 mmol) in toluene (3 ml) in sealed-tube was heated at 100° C. overnight. The solvent was removed and the residue was purified by flash column chromatography on silica gel to yield Compound 13 (81 mg, 35%).

$^1$H NMR (600 MHz, CDCl$_3$) d 11.23 (br. s., 1H), 8.14 (d, J=2.05 Hz, 1H), 7.74-7.96 (m, 2H), 7.59-7.73 (m, 1H), 7.33-7.57 (m, 5H), 7.29 (dd, J=8.22, 12.91 Hz, 1H), 7.08 (d, J=8.22 Hz, 1H), 3.98-4.08 (m, 1H), 3.80-3.93 (m, 1H), 1.30 (t, J=7.04 Hz, 3H).

Compounds 14 and 15 were prepared according to procedure F, as described in Example 7.

Compound 14

Ethyl [4-chloro-2-({[4-chloro-3-(trifluoromethyl)phenyl]sulfonyl}amino)phenyl](2,5-dimethylphenyl)phosphinate

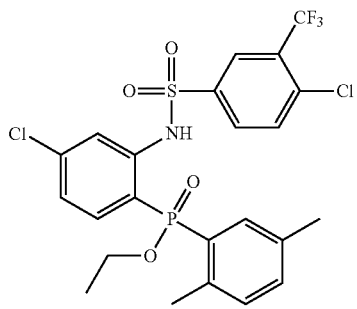 [SMILES: CCOP(=O)(c1cc(C)ccc1C)c1ccc(Cl)cc1NS(=O)(=O)c1ccc(Cl)c(C(F)(F)F)c1]

Compound 14 (78 mg, 34%) was prepared from Intermediate 1 (200 mg, 0.403 mmol) and ethyl (2,5-dimethylphenyl)phosphinate (CAS 16391-16-5) (80 mg, 0.403 mmol).

$^1$H NMR (600 MHz, CDCl$_3$) δ: 11.54 (s, 1H), 8.21 (d, J=2.05 Hz, 1H), 7.98 (dd, J=2.20, 8.36 Hz, 1H), 7.84 (dd, J=1.76, 4.40 Hz, 1H), 7.51 (d, J=8.22 Hz, 1H), 7.17-7.35 (m, 2H), 6.92-7.14 (m, 3H), 4.00-4.10 (m, 1H), 3.62-3.85 (m, 1H), 2.28 (s, 3H), 2.23 (s, 3H), 1.29 (t, J=7.04 Hz, 3H).

Compound 15

4-Chloro-N-[5-chloro-2-(dimethylphosphoryl)phenyl]-3-(trifluoromethyl)benzenesulfonamide

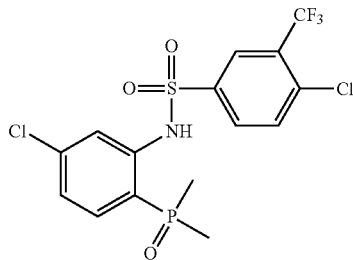 [SMILES: CP(C)(=O)c1ccc(Cl)cc1NS(=O)(=O)c1ccc(Cl)c(C(F)(F)F)c1]

Compound 15 (34 mg, 18%) was prepared from Intermediate 1 (210 mg, 0.423 mmol) and dimethylphosphine oxide (CAS 7211-39-4) (excess).

$^1$H NMR (300 MHz, CD$_3$OD) δ 8.15 (s, 1H), 8.04 (dd, J=1.76, 8.50 Hz, 1H), 7.83 (d, J=8.50 Hz, 1H), 7.64 (br. s., 1H), 7.47 (dd, J=8.35, 13.33 Hz, 1H), 7.22 (br. s., 1H), 1.68 (d, J=13.77 Hz, 6H).

General Procedure G

Example 8

Compound 16

[4-Chloro-2-({[4-chloro-3-(trifluoromethyl)phenyl]sulfonyl}amino)phenyl]phenylphosphinic acid

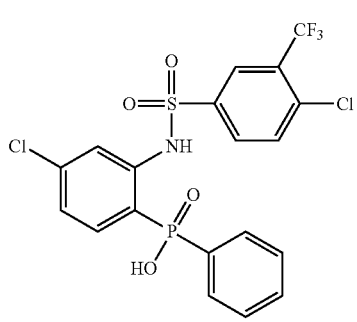 [SMILES: O=P(O)(c1ccccc1)c1ccc(Cl)cc1NS(=O)(=O)c1ccc(Cl)c(C(F)(F)F)c1]

To a solution of Compound 13 (32 mg, 0.059 mmol) in CHCl$_3$ (3 ml) was added TMSBr (1.5 ml) at room temperature. After the mixture was heated at 70° C. for 2 hours, the reaction was quenched with aq. Na$_2$SO$_3$ and was extracted with CH$_2$Cl$_2$ (2×5 ml). The combined organic layer was washed with brine and dried over Na$_2$SO$_4$ and concentrated in vacuo. The crude residue was purified by flash column chromatography on silica gel (10% MeOH in CH$_2$Cl$_2$) to afford Compound 16 as a white solid (25 mg, 83%).

$^1$H NMR (600 MHz, acetone-d$_6$) δ 8.13 (d, J=1.76 Hz, 1H), 8.05 (dd, J=1.91, 8.36 Hz, 1H), 7.67 (d, J=8.22 Hz, 1H), 7.52-7.63 (m, 2H), 7.40-7.50 (m, 2H), 7.24-7.34 (m, 1H), 7.17 (d, J=5.28 Hz, 2H), 6.92 (d, J=7.63 Hz, 1H).

Compound 17 was prepared according to procedure G, as described in Example 8.

Compound 17

[4-Chloro-2-({[4-chloro-3-(trifluoromethyl)phenyl]sulfonyl}amino)phenyl](2,5-dimethylphenyl)phosphinic acid

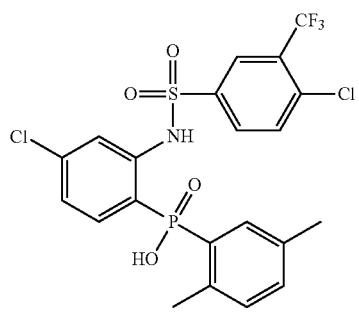 [SMILES: Cc1ccc(C)c(P(=O)(O)c2ccc(Cl)cc2NS(=O)(=O)c2ccc(Cl)c(C(F)(F)F)c2)c1]

Compound 17 (38 mg, 100%) was prepared from Compound 14.

$^1$H NMR (600 MHz, CD$_3$OD) δ 8.09 (br. s., 1H), 7.96 (br. s., 1H), 7.77 (br. s., 1H), 7.67 (d, J=8.22 Hz, 1H), 7.40 (d, J=12.91 Hz, 1H), 7.24-7.34 (m, 1H), 7.21 (d, J=7.34 Hz, 1H), 6.98-7.14 (m, 2H), 2.26 (s, 3H), 2.15 (s., 3H).

Biological Data

HEK-Gqi5 cells stably expressing CCR$_2$ were cultured in (DMEM high glucose, 10% FBS, 1% PSA, 400 μg/ml geneticin and 50 μg/ml hygromycin. Appropriate positive control chemokines (MCP-1, MIP1A or RANTES) was used as the positive control agonist for screening compound-induced calcium activity assayed on the FLIPR$^{Tetra}$. The drug plates were prepared in 384-well microplates using the EP3 and the MultiPROBE robotic liquid handling systems. Compounds were synthesized and tested for CCR$_2$ activity.

Table 1 shows activity: CCR$_2$ receptor (IC$_{50}$) nM

TABLE 1

| Compound Name | CCR$_2$ IC50 (nM) | CCR$_2$ % ANTAGONISM |
| --- | --- | --- |
| ethyl [4-chloro-2-({[4-chloro-3-(trifluoromethyl)phenyl]sulfonyl}amino)phenyl]methylphosphinate | 159 | 80 |
| 4-chloro-N-{5-chloro-2-[methyl(morpholin-4-yl)phosphoryl]phenyl}-3-(trifluoromethyl)benzenesulfonamide | 15 | 93 |

TABLE 1-continued

| Compound Name | CCR$_2$ IC50 (nM) | CCR$_2$ % ANTAGONISM |
|---|---|---|
| 4-chloro-N-{5-chloro-2-[methyl(4-oxopiperidin-1-yl)phosphoryl]phenyl}-3-(trifluoromethyl)benzenesulfonamide | 25 | 87 |
| butyl [4-chloro-2-({[4-chloro-3-(trifluoromethyl)phenyl]sulfonyl}amino)phenyl](4-oxopiperidin-1-yl)phosphinate | 537 | 84 |
| ethyl [4-chloro-2-({[4-chloro-3-(trifluoromethyl)phenyl]sulfonyl}amino)phenyl]morpholin-4-ylphosphinate | 150 | 65 |
| methyl [4-chloro-2-({[4-chloro-3-(trifluoromethyl)phenyl]sulfonyl}amino)phenyl](4-oxopiperidin-1-yl)phosphinate | 124 | 95 |
| 4-chloro-N-[5-chloro-2-(dimethylphosphoryl)phenyl]-3-(trifluoromethyl)benzenesulfonamide | 125 | 92 |

What is claimed is:

1. A compound having Formula I, its enantiomers, diastereoisomers, tautomers or a pharmaceutically acceptable salt thereof:

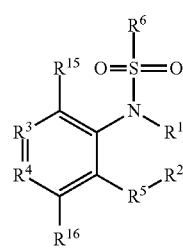

Formula I wherein:
R$^1$ is H or substituted or unsubstituted C$_{1-6}$ alkyl;
R$^2$ is substituted or unsubstituted C$_{1-6}$ alkyl, substituted or unsubstituted OC$_{1-6}$ alkyl, substituted or unsubstituted heterocycle, substituted or unsubstituted C$_{3-8}$ cycloalkyl, substituted or unsubstituted C$_{3-8}$ cycloalkenyl or substituted or unsubstituted C$_{6-10}$ aryl;
R$^3$ is C—R$^7$;
R$^4$ is C—R$^8$;
R$^5$ is —P(O)R$^{10}$;
R$^6$ is substituted or unsubstituted C$_{1-6}$ alkyl, substituted or unsubstituted heterocycle, substituted or unsubstituted C$_{3-8}$ cycloalkyl, substituted or unsubstituted C$_{3-8}$ cycloalkenyl or substituted or unsubstituted C$_{6-10}$ aryl;
R$^7$ is H, substituted or unsubstituted C$_{1-6}$ alkyl, substituted or unsubstituted heterocycle, substituted or unsubstituted C$_{3-8}$ cycloalkyl, substituted or unsubstituted C$_{3-8}$ cycloalkenyl or substituted or unsubstituted C$_{6-10}$ aryl, halogen, substituted or unsubstituted —OC$_{1-6}$ alkyl, CN, C$_{2-6}$ alkenyl, C$_{2-6}$ alkynyl, C(O)R$^{12}$, NR$^{13}$R$^{14}$ or hydroxyl;
R$^8$ is H, substituted or unsubstituted C$_{1-6}$ alkyl, halogen, -substituted or unsubstituted OC$_{1-6}$ alkyl, CN, C$_{2-6}$ alkenyl, C$_{2-6}$ alkynyl or C(O)R$^{12}$;
R$^{10}$ is H, substituted or unsubstituted C$_{1-6}$ alkyl, OH, OC$_{1-6}$ alkyl or HNC$_{1-3}$ alkyl;
R$^{12}$ is H or substituted or unsubstituted C$_{1-6}$ alkyl;
R$^{13}$ is H or substituted or unsubstituted C$_{1-6}$ alkyl;
R$^{14}$ is H or substituted or unsubstituted C$_{1-6}$ alkyl;
R$^{15}$ is H, substituted or unsubstituted C$_{1-6}$ alkyl, halogen, —OC$_{1-6}$ alkyl, CN, C$_{2-6}$ alkenyl, C$_{2-6}$ alkynyl, C(O)R$^{12}$, NR$^{13}$R$^{14}$ or hydroxyl; and
R$^{16}$ is H, substituted or unsubstituted C$_{1-6}$ alkyl, halogen, —OC$_{1-6}$ alkyl, CN, C$_{2-6}$ alkenyl, C$_{2-6}$ alkynyl, C(O)R$^{12}$, NR$^{13}$R$^{14}$ or hydroxyl.

2. A compound according to claim 1 wherein:
R$^1$ is H;
R$^2$ is substituted or unsubstituted C$_{1-6}$ alkyl, substituted or unsubstituted OC$_{1-6}$ alkyl, substituted or unsubstituted heterocycle or substituted or unsubstituted phenyl;
R$^3$ is C—R$^7$;
R$^4$ is C—R$^8$;
R$^5$ is —P(O)R$^{10}$;
R$^6$ is substituted or unsubstituted phenyl;
R$^7$ is H, substituted or unsubstituted C$_{1-6}$ alkyl or halogen;
R$^8$ is H, substituted or unsubstituted C$_{1-6}$ alkyl or halogen;
R$^{10}$ is substituted or unsubstituted C$_{1-6}$ alkyl, OH or substituted or unsubstituted OC$_{1-6}$ alkyl;
R$^{15}$ is H; and
R$^{16}$ is H.

3. A compound according to claim 2 wherein:
R$^2$ is n-butoxy, 4-oxopiperidin-1-yl, morpholin-4-yl, phenyl, methyl, 2,5-dimethylphenyl or methoxy.

4. A compound according to claim 2 wherein:
R$^{10}$ is n-butoxy, OH, ethoxy or methyl.

5. A compound according to claim 2 wherein:
R$^7$ is halogen.

6. A compound according to claim 5 wherein:
R$^7$ is chlorine.

7. A compound according to claim 2 wherein:
R$^6$ is substituted or unsubstituted phenyl.

8. A compound according to claim 7 wherein:
R$^6$ is 4-chloro-3-trifluoromethylphenyl.

9. A compound according to claim 2 wherein:
R$^1$ is H;
R$^2$ is n-butoxy, 4-oxopiperidin-1-yl, morpholin-4-yl, phenyl, methyl, 2,5-dimethylphenyl or methoxy;
R$^3$ is C—R$^7$;
R$^4$ is C—R$^8$;
R$^5$ is —P(O)R$^{10}$;
R$^6$ is 4-chloro-3-trifluoromethylphenyl;
R$^7$ is chlorine;
R$^8$ is H;
R$^{10}$ is n-butoxy, OH, ethoxy or methyl;
R$^{15}$ is H; and
R$^{16}$ is H.

10. A compound according to claim 1 selected from:
Ethyl [4-chloro-2-({[4-chloro-3-(trifluoromethyl)phenyl]sulfonyl}amino)phenyl]methylphosphinate;
Dibutyl [4-chloro-2-({[4-chloro-3-(trifluoromethyl)phenyl]sulfonyl}amino)phenyl]phosphonate;
Diethyl (4-chloro-2-(4-chloro-3-(trifluoromethyl)phenylsulfonamido)phenyl) phosphonate;
Methyl hydrogen [4-chloro-2-({[4-chloro-3-(trifluoromethyl)phenyl]sulfonyl}amino)phenyl]phosphonate;
[4-Chloro-2-({[4-chloro-3-(trifluoromethyl)phenyl]sulfonyl}amino) phenyl]methylphosphinic acid;
4-Chloro-N-{5-chloro-2-[methyl(morpholin-4-yl)phosphoryl]phenyl}-3-(trifluoromethyl)benzenesulfonamide;
4-chloro-N-{5-chloro-2-[methyl(4-oxopiperidin-1-yl)phosphoryl]phenyl}-3-(trifluoromethyl)benzenesulfonamide;
butyl hydrogen [4-chloro-2-({[4-chloro-3-(trifluoromethyl)phenyl]sulfonyl}amino)phenyl]phosphonate;
ethyl hydrogen (4-chloro-2-(4-chloro-3-(trifluoromethyl)phenylsulfonamido)phenyl)phosphonate;

butyl [4-chloro-2-({[4-chloro-3-(trifluoromethyl)phenyl]sulfonyl}amino)phenyl](4-oxopiperidin-1-yl)phosphinate;

ethyl [4-chloro-2-({[4-chloro-3-(trifluoromethyl)phenyl]sulfonyl}amino)phenyl]morpholin-4-ylphosphinate;

methyl [4-chloro-2-({[4-chloro-3-(trifluoromethyl)phenyl]sulfonyl}amino)phenyl](4-oxopiperidin-1-yl)phosphinate;

Ethyl (4-chloro-2-(4-chloro-3-(trifluoromethyl)phenylsulfonamido)phenyl)(phenyl)phosphinate;

ethyl [4-chloro-2-({[4-chloro-3-(trifluoromethyl)phenyl]sulfonyl}amino)phenyl](2,5-dimethylphenyl)phosphinate;

4-chloro-N-[5-chloro-2-(dimethylphosphoryl)phenyl]-3-(trifluoromethyl)benzenesulfonamide;

[4-Chloro-2-({[4-chloro-3-(trifluoromethyl)phenyl]sulfonyl}amino)phenyl]phenylphosphinic acid; and

[4-chloro-2-({[4-chloro-3-(trifluoromethyl)phenyl]sulfonyl}amino)phenyl](2,5-dimethylphenyl)phosphinic acid.

11. A pharmaceutical composition comprising as active ingredient a therapeutically effective amount of a compound according to claim 1 and a pharmaceutically acceptable adjuvant, diluents or carrier.

12. A pharmaceutical composition according to claim 11 wherein the compound is selected from:

Ethyl [4-chloro-2-({[4-chloro-3-(trifluoromethyl)phenyl]sulfonyl}amino)phenyl]methylphosphinate;

Dibutyl [4-chloro-2-({[4-chloro-3-(trifluoromethyl)phenyl]sulfonyl}amino)phenyl]phosphonate;

Diethyl (4-chloro-2-(4-chloro-3-(trifluoromethyl)phenylsulfonamido)phenyl) phosphonate;

Methyl hydrogen [4-chloro-2-({[4-chloro-3-(trifluoromethyl)phenyl]sulfonyl}amino)phenyl]phosphonate;

[4-Chloro-2-({[4-chloro-3-(trifluoromethyl)phenyl]sulfonyl}amino) phenyl]methylphosphinic acid;

4-Chloro-N-{5-chloro-2-[methyl(morpholin-4-yl)phosphoryl]phenyl}-3-(trifluoromethyl)benzenesulfonamide;

4-chloro-N-{5-chloro-2-[methyl(4-oxopiperidin-1-yl)phosphoryl]phenyl}-3-(trifluoromethyl)benzenesulfonamide;

butyl hydrogen [4-chloro-2-({[4-chloro-3-(trifluoromethyl)phenyl]sulfonyl}amino)phenyl]phosphonate;

ethyl hydrogen (4-chloro-2-(4-chloro-3-(trifluoromethyl)phenylsulfonamido)phenyl)phosphonate;

butyl [4-chloro-2-({[4-chloro-3-(trifluoromethyl)phenyl]sulfonyl}amino)phenyl](4-oxopiperidin-1-yl)phosphinate;

ethyl [4-chloro-2-({[4-chloro-3-(trifluoromethyl)phenyl]sulfonyl}amino)phenyl]morpholin-4-ylphosphinate;

methyl [4-chloro-2-({[4-chloro-3-(trifluoromethyl)phenyl]sulfonyl}amino)phenyl](4-oxopiperidin-1-yl)phosphinate;

Ethyl (4-chloro-2-(4-chloro-3-(trifluoromethyl)phenylsulfonamido)phenyl)(phenyl)phosphinate;

ethyl [4-chloro-2-({[4-chloro-3-(trifluoromethyl)phenyl]sulfonyl}amino)phenyl](2,5-dimethylphenyl)phosphinate;

4-chloro-N-[5-chloro-2-(dimethylphosphoryl)phenyl]-3-(trifluoromethyl)benzenesulfonamide;

[4-Chloro-2-({[4-chloro-3-(trifluoromethyl)phenyl]sulfonyl}amino)phenyl]phenylphosphinic acid;

[4-chloro-2-({[4-chloro-3-(trifluoromethyl)phenyl]sulfonyl}amino)phenyl](2,5-dimethylphenyl)phosphinic acid.

13. A method of treating an ocular inflammatory disease or skin inflammatory disease by antagonizing CCR2, which comprises administering to a mammal in need thereof, a pharmaceutical composition comprising a therapeutically effective amount of at least one compound of Formula I

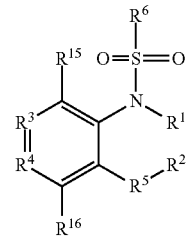

Formula I wherein:
$R^1$ is H;
$R^2$ is substituted or unsubstituted $C_{1-6}$ alkyl, substituted or unsubstituted $OC_{1-6}$ alkyl, substituted or unsubstituted heterocycle or substituted or unsubstituted phenyl;
$R^3$ is C—$R^7$;
$R^4$ is C—$R^8$;
$R^5$ is —P(O)$R^{10}$;
$R^6$ is substituted or unsubstituted phenyl;
$R^7$ is H, substituted or unsubstituted $C_{1-6}$ alkyl or halogen;
$R^8$ is H, substituted or unsubstituted $C_{1-6}$ alkyl or halogen;
$R^{10}$ is substituted or unsubstituted $C_{1-6}$ alkyl, OH or substituted or unsubstituted $OC_{1-6}$ alkyl;
$R^{15}$ is H; and
$R^{16}$ is H.

14. The method of claim 13 wherein the mammal is a human.

* * * * *

UNITED STATES PATENT AND TRADEMARK OFFICE
CERTIFICATE OF CORRECTION

PATENT NO. : 8,518,913 B2
APPLICATION NO. : 13/315514
DATED : August 27, 2013
INVENTOR(S) : Haiqing Yuan et al.

It is certified that error appears in the above-identified patent and that said Letters Patent is hereby corrected as shown below:

On the title page, in Item (56), under "Other Publications", in column 2, line 32, delete "Scadinavica," and insert -- Scandinavica --, therefor.

On title page 2, in column 1, Item (56), under "Other Publications", line 6, delete "Dextan" and insert -- Dextran --, therefor.

In the Specification

In column 1, line 7, delete "2011," and insert -- 2010, --, therefor.

In column 1, line 40, delete "atheroscelorsis" and insert -- atherosclerosis --, therefor.

In column 4, line 3, delete "–P(O)R$^{16}$;" and insert -- –P(O)R$^{10}$; --, therefor.

In column 5, line 34, delete "form" and insert -- from --, therefor.

In column 5, line 44, delete "pyrazol," and insert -- pyrazole, --, therefor.

In column 5, lines 46-47, delete "thiazole1-H-pyrazole," and insert -- thiazole, 1H-pyrazole, --, therefor.

In column 7, line 30, delete "Stahal" and insert -- Stahl --, therefor.

In column 7, line 31, delete "Chemica Acta-" and insert -- Chimica Acta- --, therefor.

In column 7, line 39, delete "Stahal" and insert -- Stahl --, therefor.

In column 7, line 40, delete "Chemica Acta-" and insert -- Chimica Acta- --, therefor.

In column 8, line 9, delete "orchiectomyatopic" and insert -- orchiectomy atopic --, therefor.

In column 8, line 58, delete "(PONS)," and insert -- (POHS), --, therefor.

In column 9, line 64, delete "(PONS)," and insert -- (POHS), --, therefor.

In column 13, line 23, delete "diasteroisomeric" and insert -- diastereoisomeric --, therefor.

In column 15, lines 40-41, delete "ethylenediame" and insert -- ethylenediamine --, therefor.

In column 16, lines 1-2, delete "ethylenediame" and insert -- ethylenediamine --, therefor.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,518,913 B2

In column 16, lines 29-30, delete "dimethylethylenediame" and insert -- dimethylethylenediamine --, therefor.

In column 18, lines 4-5, delete "(m, J=6.16, 6.16," and insert -- (m, J=6.16, --, therefor.

In the Claims

In column 23, line 58, in claim 1, delete "-substituted" and insert -- substituted --, therefor.